(12) United States Patent
Yoo et al.

(10) Patent No.: US 6,566,545 B2
(45) Date of Patent: May 20, 2003

(54) MENTHOL DERIVATIVES AND PROCESS FOR PREPARING THE SAME

(75) Inventors: Jae Won Yoo, Seoul (KR); Duck Hee Kim, Seoul (KR); Seong Joon Moon, Kyunggi-do (KR); Min Soo Noh, Seoul (KR); Soo Hyun Kim, Seoul (KR); Su Sun An, Seoul (KR); Jin Seon Lee, Kyunggi-do (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 10/226,129

(22) Filed: Aug. 23, 2002

(65) Prior Publication Data
US 2003/0069209 A1 Apr. 10, 2003

(30) Foreign Application Priority Data
Aug. 27, 2001 (KR) .......................................... 2001-51782

(51) Int. Cl.$^7$ .................................................. C07F 9/02
(52) U.S. Cl. ............................ 558/89; 558/87; 558/166
(58) Field of Search ............................ 558/87, 89, 166

(56) References Cited

U.S. PATENT DOCUMENTS

| | | | | |
|---|---|---|---|---|
| 3,917,613 A | * | 11/1975 | Humbert et al. | 260/293.65 |
| 3,991,178 A | * | 11/1976 | Humbert et al. | 424/54 |
| 5,723,645 A | | 3/1998 | Lee et al. | 558/132 |
| 5,883,084 A | | 3/1999 | Peterson et al. | 514/78 |
| 5,916,915 A | | 6/1999 | Hong et al. | 514/474 |

FOREIGN PATENT DOCUMENTS

| | | |
|---|---|---|
| EP | 0 273 266 A2 | 7/1988 |
| WO | WO 92/06947 | 4/1992 |

* cited by examiner

Primary Examiner—Raymond Henley, III

(57) ABSTRACT

The present invention provides a menthol derivative represented by the following Formula 1 and a method for preparing the menthol derivative. The menthol derivative represented by the Formula 1 is prepared by reacting menthol and phosphorous oxychloride with an equivalence ratio of 1:1~1.3 in an organic solvent in the presence of organic base to obtain dichloro[5-methyl-2(mehtylethyl)cylclohexyloxy]phosphino-1-one; and reacting above obtained dichloro[5-methyl-2(mehtylethyl)cylclohexyloxy]phosphino-1-one with 3-amino propanol in the organic solvent in the presence of the organic; then hydrolyzing and crystallizing the product with polar organic solvent.

[Formula 1]

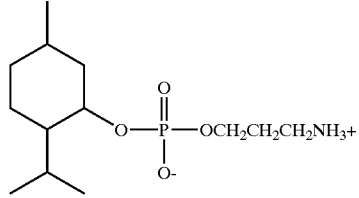

7 Claims, 1 Drawing Sheet

FIGURES

MENTHOL DERIVATIVES AND PROCESS FOR PREPARING THE SAME

BACKGROUND OF THE INVENTION

1. Field of the Invention

The present invention relates to a menthol derivative represented by the following Formula 1 and a method for preparing the menthol derivative. More particularly, the present invention relates to a menthol derivative wherein menthol and 3-aminopropylphosphoric acid form a phospho-diester bond, and therefore, it can be decomposed by the enzyme to exhibit both the activities of menthol and 3-aminopropylphosphoric acid in the living body.

[Formula 1]

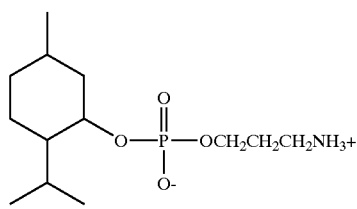

2. Description of the Related Arts

Menthol is known as a main component of peppermint, and the peppermint is a well-known fragrant plant. According to oriental medicine, the peppermint has effects of clearing and suppressing cold, and, because it has heat dispelling and perspiration effects, it has been used for itching, pains such as arthritis and neuralgia, tuberculosis and gastroenteric disorder, etc. Further, because it shows the effects on central blood vessel and relaxation of blood vessel, it has been used for paralysis. And, peppermint tea is known as good for stress and nervousness.

These effects of the peppermint seem to originate from L-menthol, the main component of peppermint. L-menthol is expressed chemically as $C_{15}H_{20}O$ and transparent needle-shaped crystal with fresh fragrance. It is not dissolved in aqueous phase (water), but well dissolved in ethanol, ether and chloroform. The menthol having these features is obtained from extraction of peppermint stems or leaves and synthesized chemically by adding water to the ketones or double bond compounds such as menthone, fragone, piperitone, thymol and isofragone.

The effects of menthol are well known in the modern medicine as well oriental medicine. L-menthol reduces the irritation of skin due to the effect of local anesthesia, and its derivative is reported to have an anti-inflammation effect. Further, it has an antibacterial effect.

Since the menthol has a lot of useful effects as seen above, it is used for toothpaste, jam, candy, tobacco, etc. However, it has not widely used in the field of cosmetics because it has strong fragrance and irritation on the eye. To overcome this problem, there were many studies to prepare menthol derivatives. For example, ester derivative of menthol has the effects of reducing the strong fragrance and irritation on the eye, but on the other hand, its useful effects also reduced.

Under this condition, the inventors of the present invention tried and studied to develop menthol derivatives to overcome the above problems. As the result, a menthol derivative obtained from phospho-diester of menthol and 3-amino propylphosphoric acid, a component used for anti-aging cosmetic composition, was found to reduce the irritation of menthol while maintaining the useful effects of menthol and found to show both the physiological effects of menthol itself and 3-aminopropylphosphoric acid when applied to living body.

SUMMARY OF THE INVENTION

The object of the present invention is to provide a menthol derivative with reduced irritation by comprising phosphorous group therein.

Further, another object of the present invention is to provide a method for preparing menthol derivative comprising phosphorous group.

To accomplish the above objects, the present invention provides a menthol derivative represented by the following Formula 1.

[Formula 1]

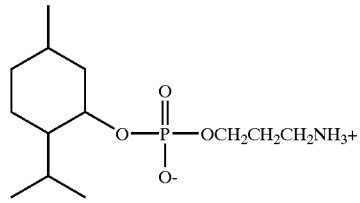

The above menthol derivative has reduced irritation compared with menthol itself, but has all the physiological effects of the menthol.

Further, the above menthol derivative is easily decomposed in the human body by the enzyme, and exhibits both the physiological activities of menthol and 3-aminopropylphosphoric acid.

Further, the present invention provides a method for preparing menthol derivative and its salt, by reacting menthol and phosphorous oxychloride in an organic solvent in the presence of organic base, further reacting with 3-amino propanol in the organic solvent in the presence of the organic base, then hydrolyzing and crystallizing the reaction resultant to obtain menthol derivative and the salt thereof.

More particularly, the method of the present invention comprises the steps of;

(A) reacting menthol and phosphorous oxychloride with an equivalence ratio of 1:1~1.3 in an organic solvent in the presence of organic base at 12~18° C. for 1~2 hours to obtain dichloro[5-methyl-2(mehtylethyl) cylclohexyloxy]phosphino-1-one;

(B) reacting above obtained dichloro[5-methyl-2 (mehtylethyl)cylclohexyloxy]phosphino-1-one with 3-amino propanol in the organic solvent in the presence of the organic base to obtain 2[5-methyl-2-(methylethyl)cyclohexyloxy]-1,3,2-oxazaphosphorine P-oxide;

(C) filtering the reaction resultant of step (B), and concentrating the filtrate under reduced pressure, then adding acid solution to the concentrated product and reacting at 5~100° C. for 3~12 hours for hydrolysis; and (D) crystallizing the product of step (C) with polar and organic solvent.

The present invention is described in detail hereinafter.

The method for preparing the menthol derivative of the present invention is schematized by the following Reaction Scheme 1.

[Reaction Sheme 1]

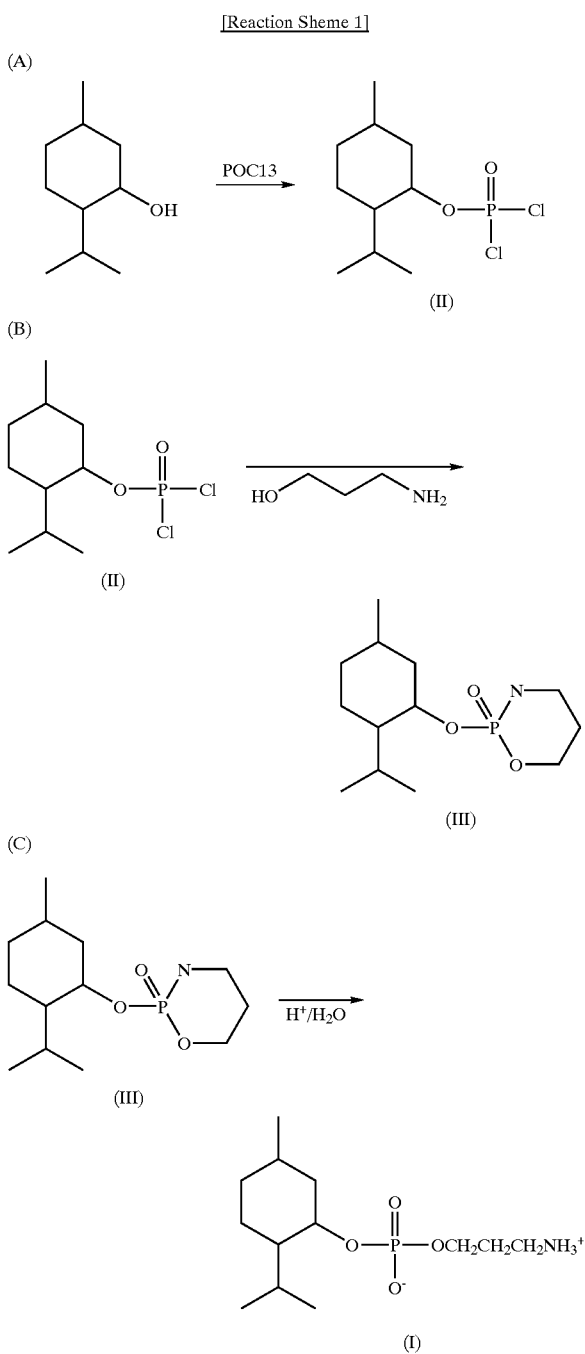

Each steps of the method for preparing the menthol derivative of the present invention is described hereinafter.

Step (A): reacting menthol and phosphorous oxychloride in an organic solvent in the presence of an organic base at 12~18° C. for 1~2 hours to obtain dichloro[5-methyl-2(mehtylethyl)cylclohexyloxy]phosphino-1-one represented by structural formula (II) of the above Reaction Scheme 1.

In step (A), the equivalence ratio of menthol and phosphorous oxychloride is preferably 1:1~1.3. When the equivalence ratio is less than 1:1, the object material is not obtained; while, when the equivalence ratio is more than 1:1.3, an excessive amount of by-products are obtained. Therefore, when menthol and phosphorous oxychloride is reacted with the equivalence ratio of 1:1~1.3, the product, dichloro[5-methyl-2(mehtylethyl)cylclohexyloxy] phosphino-1-one in which menthol and phosphorous oxychloride is bonded with a ratio of 1:1 is obtained about 95%, and a by-product in which menthol and phosphorous oxychloride is bonded with a ratio of 2:1 is obtained less than 1~2%. Further, because that amount of by-product is removed by chromatography or by the separation method using the difference of solubility in toluene, the equivalence ratio of menthol and phosphorous oxychloride is preferably 1:1~1.3.

The reaction is preferably performed at 12~18° C. for 1~2 hours, which can inhibit the production of by-product tha menthol and phosphorous oxychloride are bonded with a ratio of 2:1 or more; and especially, introducing ester group or amide group to protect a chlorine atom in the oxychloride is not needed, which makes the process simple.

The base used in step (A) comprises organic base such as pyridine and triethylamine; and triethylamine is preferable.

The organic solvent in step (A) comprises dichloromethane, tetrahydrofuran, ethyl acetate, acetonitrile, chloroform, ethylether, trichloro ethylene, benzene, toluene, etc.; and toluene is preferable.

The reaction temperature is preferably 12~18° C. When the temperature is more than 18° C., two or more equivalent amount of menthol is bonded to one equivalence of phosphorous oxychloride, which increase the by-product; while, when the reaction temperature is less than 12° C., reaction rate decreases to make the reaction difficult and the yield decreases because non reacted components increases.

Step (B): reacting above obtained dichloro[5-methyl-2 (mehtylethyl) cylclohexyloxy]phosphino-1-one and 3-aminopropanol in an organic solvent in the presence of an organic base.

The base used in step (B) comprises organic base such as pyridine and triethylamine that used in step (A), further, such bases as sodiumhydroxide and potassiumhydroxide may be used. Preferably, triethylamine is used.

The organic solvent in step (B) comprises inert solvents such as dichloromethane, tetrahydrofuran, ethyl acetate, acetonitrile, chloroform, ethylether, etc., and polar solvent such as methanol, ethanol, propanol, etc. Preferably, tetrahydrofuran is used.

Step (C): filtering the reaction resultant obtained in step (B) then concentrating the filtrate under reduced pressure, and adding acid solution to the residue (concentrated product above), and reacting at 5~100° C. for 3~12 hours for hydrolysis.

The hydrolysis of the residue obtained by filtering the reaction resultant of step (B) and concentrating the filtrate under reduced pressure may be performed in general hydrolysis condition, that is, the hydrolysis may be performed by using acid catalysis such as strong acid cation (SAC) ion exchange resin, hydrochloric acid or sulfuric acid.

In detail, after adding acid solution to the compound obtained in step (B), the mixture is stirred while increasing the temperature up to 5~100° C. to hydrolyze the P—N bonding. Preferably, the hydrolysis can be performed proceeding the following steps of; filtering the reaction resultant of step (B) and concentrating the filtrate under reduced pressure to obtain a residue (concentrated product), then adding acid solution to the residue and reacting at 5~100° C., preferably at 40~60° C., for 3~12 hours, preferably for 8~12 hours. The acidity of the acid solvent is pH 1~5, preferably pH 2~4.

Step (D): crystallizing the above-obtained menthol 3-aminopropanol phospho-diester (menthol 3-aminopropylphosphate) by adding polar and organic solvent.

The solvent used in step (D) is not limited specifically, but preferably methanol, ethanol, isopropanol, acetone, tetrahydrofuran, acetonitrile or dioxane may be used.

The menthol derivative obtained above may be used as salt type after neutralization, for example, alkali metal salt type such as sodium salt, potassium salt, etc. is preferable usage type.

The menthol derivative and its salts of the present invention may be used for cosmetic composition and pharmaceutical composition. The amount of the menthol derivative or its salt for the cosmetic composition may be 0.001~30 wt. % to the weight of total composition. Further, in case that menthol derivative or its salt of the present invention is used for pharmaceutical composition, a person skilled in the art can determine the amount needed according to the state of the patient or the disease, and also can make preferable formulation thereof without difficulty.

Figure 1:
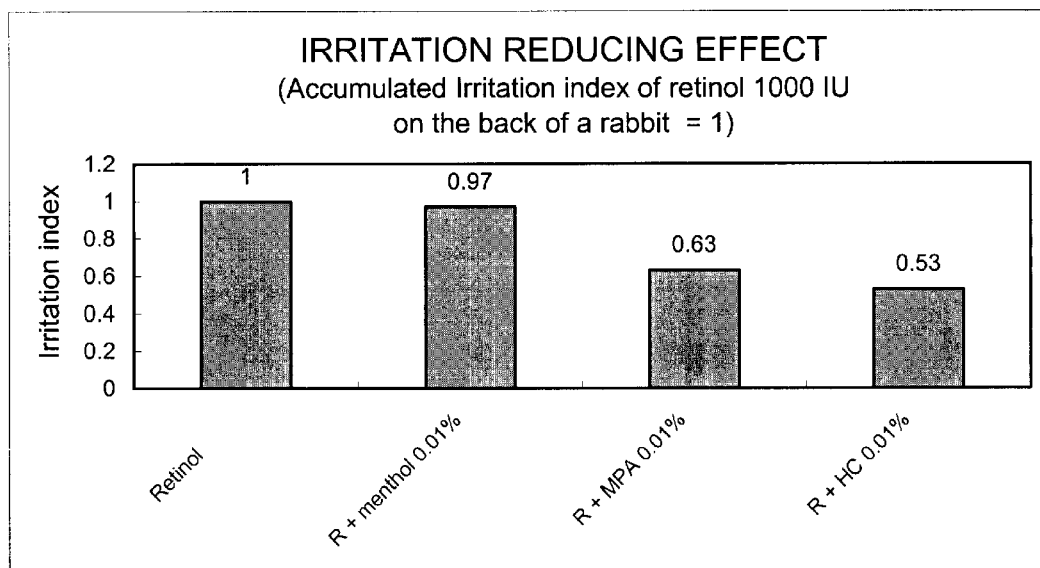
FIG. 1 is a graph showing the effects of the menthol derivative of the present invention to reduce irritation.

Hereinafter, the present invention is described with reference to the examples, however, the scope of the present invention is not limited to the following examples.

PREFERRED EMBODIMENT OF THE INVENTION

EXAMPLE 1

Preparation of Dichloro[5-methyl-2-(methylethyl) cyclohexyloxy]phosphino-1-one 4.5 g (0.03 mol) of phosphorous oxychloride was dissolved in 10 ml of hexane, and 3 g (0.03 mol) of triethylamime and 20 ml of toluene was added thereto, then cooled in ice bath to 0~5° C. On the other hand, 3.12 g (0.02 mol) of menthol was dissolved in 80 ml (0.73 mol) of toluene, and this solution was added to the above prepared phosphorous oxychloride solution dropwisely for 2 hours. After the adding (dropwise adding), a by-product, triethylamoniumchloride was removed by filtering. The remained solution (filtrate) was washed with 100 ml of distilled water, and dried with anhydrous $Na_2SO_4$, then filtered and concentrated under reduced pressure.

As the product, 4.3 g of dichloro[5-methyl-2-(methylethyl)cyclohexyloxy]phosphino-1-one was obtained with yellow oily state.

IR($CHCl_3$, $cm^{-1}$): 3345, 2950, 2764, 1460, 1374, 1092, 1046, 996;

1H-NMR($CDCl_3$): δ (ppm)=0.74(d, 3H), 0.90(d, 6H), 1.11(m, 2H), 1.32(d, 2H), 1.65(d, 2H), 2.05(m, 1H), 2.25(m, 1H), 4.45(m, 1H).

EXAMPLE 2

Preparation of Menthol 3-Aminopropylphosphate (Diester of Menthol and 3-Aminopropyl Phosphoric Acid)

1.8 g (1.2 eq) of 3-aminopropanol and 4.9 g of triethylamine were added to 30 ml of tetrahydrofuran, and stirred for 30 minutes in room temperature. At the same temperature, 2.39 g of dichloro[5-methyl-2-(methylethyl) cyclohexyloxy]phosphino-1-one obtained in Example 1 was added dropwisely thereto. After the adding, the mixture was stirred for one night at room temperature, then, a by-product, triethylamoniumchloride was removed. The remained solution was washed with 15% brine, and dried with anhydrous $Na_2SO_4$, and filtered. The filtrate was concentrated under reduced pressure, and recrystallized with hexane to obtain a product of 2[5-methyl-2-(methylethyl)cyclohexyloxy-5-yloxy]-1,3,2-oxazaphosphorine P-oxide with solid state.

The above product was dissolved in aqueous solution of pH 3, and stirred for 8 hours in a 40° C. thermostatic bath. After stirring, ethanol and 150 ml of acetonitrile was added thereto, and filtered then vacuum dried to obtain 2.2 g of solid menthol 3-amino propylphosphate.

IR(KBr, cm-1): 3407, 2953, 2801, 1463, 1369, 1207, 1076;

1H-NMR(D20): δ (ppm)=0.68(d, 3H), 0.74(m, 1H), 0.79 (d, 6H), 0.93(m, 2H), 1.16(m, 1H), 1.31(m, 1H), 1.54(d, 2H), 1.88(m, 2H), 1.99(m, 2H), 3.03(t, 2H), 3.90(m, 1H).

EXAMPLE 3

Preparation of Sodium Salt of Menthol 3-Aminopropyl Phosphate 1 g of menthol 3-aminopropylphosphate obtained in the example 2 was dissolved in 30 ml of distilled water, then 5% aqueous solution of sodium carbonate was added to neutralize the solution with pH 7. The solution was freeze dried to obtain sodium salt of menthol 3-aminopropylphosphate with pale yellow solid state.

1H-NMR(D20): δ (ppm)=0.68(d, 3H), 0.76(m, 1H), 0.80 (d, 6H), 0.91(m, 2H), 1.18(m, 1H), 1.31(m, 1H), 1.56(d, 2H), 1.90(m, 2H), 2.01(m, 2H), 3.03(t, 2H), 3.91(m, 1H)

EXAMPLE 4

Preparation of Potassium Salt of Menthol 3-Aminopropyl Phosphate 1 g of menthol 3-aminopropylphosphate obtained in the example 2 was dissolved in 30 ml of distilled water, then 5% aqueous solution of potassium carbonate was added to neutralize the solution with pH 7. The solution was freeze dried to obtain potassium salt of menthol 3-aminopropylphosphate with pale yellow solid state.

1H-NMR(D20): δ (ppm)=0.68(d, 3H), 0.75(m, 1H), 0.79 (d, 6H), 0.92(m, 2H), 1.16(m, 1H), 1.32(m, 1H), 1.56(d, 2H), 1.89(m, 2H), 1.98(m, 2H), 3.01(t, 2H), 3.90(m, 1H).

EXPERIMENTAL EXAMPLE 1

The hairs on the back of New Zealand White Rabbit were removed and fed with sufficient water and nutrition. At the areas of 1.5 cm×1.5 cm on the back of the rabbit, menthol, menthol 3-aminopropylphosphate (MPA) and 1000 I.U. of retinol as irritation source were applied respectively. The number of applying positions for each rabbit was 8~10, and the agents were applied twice a day with 6 hours of time interval. The applied positions were exposed to air. Erythema, rash or edema was measured everyday after 48 hours has passed from the first apply during 1 week to observe the irritation. According to the "Primary Irritation Index" of Draize, the degree of irritation was determined. Relative irritation was calculated with the ratio to the blank sample that applied only with retinol, and the results are shown in Table 1 and FIG. 1.

TABLE 1

| | Irritation Index | Relative Ratio |
|---|---|---|
| Retinol only (Blank) | 9.63 | 1 |
| Retinol + menthol 0.01% | 9.34 | 0.97 |
| Retinol + menthol 3-aminopropyl phosphate (MPA) 0.01% | 6.07 | 0.63 |
| Retinol + hydrocortisone 0.01% | 5.10 | 0.53 |

As seen in Table 1 and FIG. 1, menthol 3-aminopropyl phosphate (MPA) showed 37% reduction of the irritation compared to the blank that applied only with retinol, and showed similar reduction of irritation with the Hydrocortisone (HC).

EXPERIMENTAL EXAMPLE 2

To observe the solubility of the menthol 3-aminopropylphosphate in the aqueous phase, solubility were measure in aqueous and aqueous mixed solution.

Menthol was used as relativity group. The results are shown table 2.

TABLE 2

| | Menthol | menthol 3-amino propylphosphate |
|---|---|---|
| H$_2$O | insoluble | 0.3% |
| H$_2$O:Ethanol = 5:1 | Insoluble | 1% |
| H$_2$O:Ethanol = 1:1 | Less than 0.05% | 6% |
| H$_2$O:1,3-BG = 1:1 | Less than 0.05% | 5% |

As seen in the above Table 2, the aqueous solubility of menthol 3-amino propylphosphate was increased very much compared with menthol itself. Therefore, aqueous product can be easily made by using the menthol derivative of the present invention.

EXPERIMENTAL EXAMPLE 3

To clarify the activity of menthol 3-aminopropylphosphate obtained in Example 2, the hydrolysis of the menthol 3-aminopropylphosphate by a phosphatase in the skin was observed. That is, the preparation of menthol and 3-aminopropylphosphoric acid by the hydrolysis was observed.

3-aminopropylphosphate and phosphatase were added to phosphoric buffer solution with pH 7.4, then, hydrolysis was performed. The phosphatase used above was Alkaline Phosphate manufactured by SIGMA, Co., Ltd.

Figure 2:
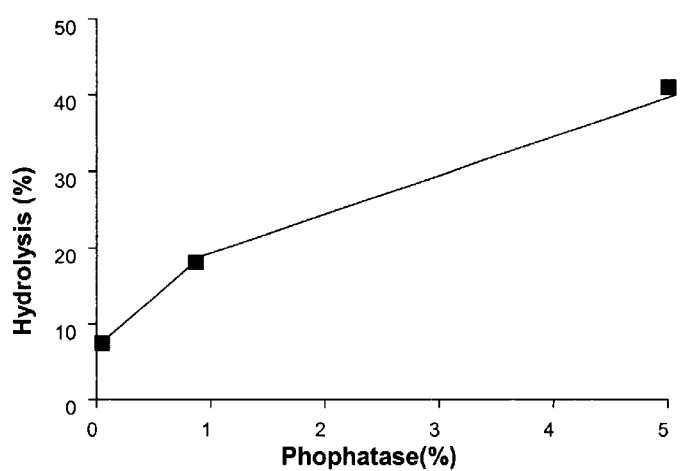
FIG. 2 is a graph showing the physiological activity of the menthol derivative of the present invention.

The amount of the 3-aminopropylphosphoric acid prepared by the hydrolysis was measured by means of HPLC, and the results are shown in FIG. 2.

As seen in FIG. 2 attached, it was affirmed that menthol 3-amino propylphosphate was hydrolyzed by the phosphatase of the skin and formed menthol and 3-aminopropylphosphoric.

The menthol derivative of the present invention, menthol 3-amino propylphosphate that is a diester of menthol and 3-aminopropylphosphoric acid, and its salt shows increased solubility and purity compared with menthol itself that are not soluble in the aqueous phase. Therefore, the menthol derivative of the present invention and its salt can be applied to aqueous formulations. Further, the menthol derivative of the present invention and its salt comprises phosphoric group that has excellent skin affinity, which increases the permeability of the skin and decrease the irritation of the skin. Therefore, the menthol derivative of the present invention is an excellent component for a cosmetic or pharmaceutical composition.

We claim:

1. A menthol derivative represented by following Formula 1.

[Formula 1]

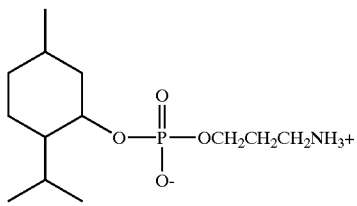

2. The menthol derivative according to claim 1, wherein said menthol derivative is prepared by reacting menthol and phosphorous oxychloride in an organic solvent in the presence of organic base, then reacting with 3-amino propanol in the organic solvent in the presence of the organic, and hydrolyzing the product, then, crystallizing the hydrolyzed product with polar organic solvent.

3. A method for preparing a menthol derivative;

(A) reacting menthol and phosphorous oxychloride with an equivalence ratio of 1:1~1.3 in an organic solvent in the presence of an organic base at 12~18° C. for 1~2 hours to obtain dichloro[5-methyl-2(mehtylethyl) cylclohexyloxy]phosphino-1-one;

(B) reacting the above obtained dichloro[5-methyl-2 (mehtylethyl)cylclohexyloxy]phosphino-1-one with 3-aminopropanol in an organic solvent in the presence of an organic base to obtain 2[5-methyl-2(methylethyl) cyclohexyloxy]-1,3,2-oxazaphosphorine P-oxide;

(C) filtering the reaction resultant of step (B) and concentrating the filtrate under reduced pressure, then adding acid solution thereto and reacting at 5~100° C. for 3~12 hours for hydrolysis; and (D) crystallizing the product of step (C) with polar organic solvent.

4. The method for preparing a menthol derivative according to claim 3, wherein said organic solvent of step (A) is at least one selected from the group consisting of dichloromethane, tetrahydrofuran, ethyl acetate, acetonitrile, chloroform, ethylether, trichloroethylene, benzene and toluene.

5. The method for preparing a menthol derivative according to claim 3, wherein said polar organic solvent of step (D) is methanol, ethanol, isopropanol, acetone, tetrahydrofuran, acetonitrile or dioxane.

6. A salt of menthol derivative prepared by combining menthol derivative of claim 1 and alkali metal.

7. The salt of menthol derivative according to claim 6, wherein said alkali metal is Na or K.

* * * * *